United States Patent [19]
Cartwright et al.

[11] Patent Number: 5,890,244
[45] Date of Patent: Apr. 6, 1999

[54] PROTECTIVE PADDED ACCESSORY FOR USE ON LONG-TERM CARE BED RAILS

[76] Inventors: Wanda K. Cartwright, 124 Oakland Dr., Gallatin, Tenn. 37066; Marlene Marlin, 300 Tyree Springs Rd., Whitehouse, Tenn. 37188

[21] Appl. No.: 65,165

[22] Filed: Apr. 23, 1998

[51] Int. Cl.$^6$ .............................. A47C 21/00; A47C 21/08
[52] U.S. Cl. ...................................................... 5/663; 5/922
[58] Field of Search ................................ 5/663, 424, 425, 5/922; 248/345.1

[56] References Cited

U.S. PATENT DOCUMENTS

| | | | |
|---|---|---|---|
| 3,742,530 | 7/1973 | Clark | 5/331 |
| 4,215,446 | 8/1980 | Mahoney | 5/425 |
| 4,523,745 | 6/1985 | Killman et al. | 5/663 |
| 4,827,545 | 5/1989 | Arp | 5/424 |
| 5,044,025 | 9/1991 | Hunsinger et al. | 5/424 |
| 5,097,550 | 3/1992 | Marra, Jr. | 5/424 |
| 5,175,897 | 1/1993 | Marra, Jr. | 5/425 |
| 5,450,641 | 9/1995 | Montgomery | 5/663 |
| 5,481,772 | 1/1996 | Glynn et al. | 5/663 |
| 5,557,817 | 9/1996 | Haddock | 5/663 |

*Primary Examiner*—Alex Grosz
*Attorney, Agent, or Firm*—Waddey & Patterson; Mark J. Patterson

[57] ABSTRACT

A bed-rail protective cover for protecting a long-term care patient in a bed having a bed-rail from injuries resulting from contact with the bed-rail. The protective cover includes: an inner surface and an outer surface composed of a material, flexible and non-abrasive, material which is substantially resistant to penetration by an appendage of a person with a fill material between the inner and outer surfaces. The cover fill is sufficient to absorb impacts to the cover and reduce risk of injury to a patient resulting from impacting a bed-rail. The cover further includes a top edge of extending sufficiently over a bed-rail to prevent a patient from inadvertently poking an appendage between the bed and the bed-rail or through a gap between two covers. A securing flap extending from the top edge overlaps and fastens to a bottom edge when the cover enfolds the bed-rail. Securing flap fasteners are located where risk of inadvertent contact with them is reduced. Means to inhibit lateral movement of the cover along the bed-rail is also disclosed. One embodiment of the cover includes cut-outs to allow access to bed-rail adjustment mechanisms. Thus allowing the bed-rail to be quickly and conveniently raised and lowered while maintaining the protective cover on the bed-rail. A recessed bed control opening is disclosed, wherein the bed control is sufficiently recessed in the opening to reduce risk of inadvertent contact by a patient.

11 Claims, 6 Drawing Sheets

PROTECTIVE PADDED ACCESSORY FOR USE ON LONG-TERM CARE BED RAILS

BACKGROUND OF THE INVENTION

This invention relates generally to padded covers used to enclose bed side rails. More particularly this invention relates to bed-rails used to improve the comfort and safety of patients in long-term care facilities. Generally, long-term care patients have more fragile bones and skin. Therefore, they generally require greater protection than is provided by standard hospital bed-rail protective coverings. Prior art has generally focused on ease of access for the nurse or doctor as well as on standardizing the shape of covers. U.S. Pat. No. 3,742,530 (Clark) exhibits a bed-rail cover of plastic or quilted cotton. Clark does not seem to be designed for a movable bed-rail. The configuration does not give adequate protection to a patient entering or exiting the bed-rail side of the bed, with the bed-rail in the down position. The side of the bed-rail which faces out is left generally exposed. This could likely prove hazardous to patients having to be quickly removed from the bed. The outside of the bed-rail would need to be padded for ingress as well as egress of a patient under long-term care.

U.S. Pat. No. 4,215,544 (Mahoney) describes a bed-rail cover which exhibits the possibility of hard spots which may injure a patient while she gets in or out of the bed. Also, limbs may be flayed against the railing during seizures or 'fits'. The potential for injury as a result of impacting a 'hard spot' increases as bones become more fragile with time. Fragile bones may be due to decreasing bone density associated with aging, for instance. 'Hard spots' are places where a hard substance is felt beneath the protective covering, or where there is no covering, and may lead to injuries to patients with fragile bones.

U.S. Pat. No. 4,827,545 (Arp) uses pre-formed pipe insulation covered by plastic with a zipper fastener. The Arp design exhibits too many 'edges' which may injure a fragile patient; 'edges' being any sharp side which may cause lacerations or abrasions to sensitive skin. Arp does not employ, nor suggest, non-abrasive coverings. Nonabrasive coverings would be beneficial in reducing scrapes and 'edge' injuries.

U.S. Pat. No. 5,044,025 (Hunsinger, et al.) displays a slip cover having a portion facing the bed interior padded with a removable bolster to inhibit tossing and turning towards the rail. This design leaves possible hard spots along the railing edge as well as impedes the ability for rapid lowering of the rail in the event of an emergency. Hunsinger seems more appropriate to preventing small children or infants from falling through bed-rails or between a bed-rail and a mattress than use with a long term care patient.

U.S. Pat. No. 5,097,550 and U.S. Pat. No. 5,175,897 (Marra, Jr.) teach a bed-rail cover system which includes a bed-rail and cover positionable over a bed-rail framework. This additionally includes equipment housing means disposed within the cover. This may provide a convenient access to control equipment, but it increases the risk of injury from hard spots or edges particularly to patients of long-term care patients. The design also does not suggest adaptation to a movable bed-rail.

U.S. Pat. No. 5,450,641 (Montgomery) is an inflatable sheet with elongated strips to provide padding. This may be acceptable for short-term occasional use (the Montgomery specification refers to ease of storage when the rail guard is not in use). This is not acceptable for long-term patient care; it lacks durability and exhibits the potential for too many hard spots as can be seen in FIGS. 3 and 4 of Montgomery.

U.S. Pat. No. 5,557,817 (Haddock) provides a protective cover for removable placement over bed-rails of a hospital bed. An objective of Haddock is to provide a cover of a standardized size. Haddock is trying to overcome use of a long cover which would require the hospital to carry short as well as long covers. Haddock designs a cover for a half bed-rail which accomplishes the objective of a standardized cover. But, the standardized cover comes at the expense of it being less suitable for long-term patient care which employs full-length bed-rails. For long rails, or full-length bed-rails, Haddock requires axially aligning the covers and affixing the fastener strips of one cover to the fastener strips of the other cover. (See FIG. 5) As can be seen from FIG. 4 or FIG. 5 of Haddock, there exists the possibility of 'edge' injury from fasteners when employing a two-cover arrangement. 'Poke-through' is also possible. 'Poke-through' is the condition of a limb or digit poking through a gap between abutting covers, or sticking out between a bed-rail and a mattress. Because patients of certain illnesses will exhibit, often times intense, thrashing of their limbs, a durable soft protective cover is needed, not a two-piece arrangement with gaps and fasteners facing the interior of the bed.

What is needed, then, is a bed-rail protective cover to provide a safe environment for the recipient of long-term care. The device must protect the patient from 'hard spots,' or spots where the hardness of the rail would injure the patient. This 'edge' injury, that is injuries due to the skin being abraded, bruised or lacerated on an edge of the cover or fastener must be avoided. Protection from 'hard spots' and 'edges' should be maintained during egress and ingress to the bed as well as when the patient is in the bed. The covering must reduce risk of 'poke-through,' that is, a limb or digit being caught between the mattress and the cover or through the cover itself. The covering should soft, well padded, nonabrasive, cleanable, and should be moisture resistant. The protective cover must not impede rapid lowering of bed-rails. The covering should be quickly and easily attachable and detachable.

SUMMARY OF THE INVENTION

The invention relates generally to bed-rail protective coverings. Specifically the invention relates to bed-rail protective covers for long-term care patients. Long-term care patients often have fragile bones which are more easily injured or skin which is more easily abraded than a short-term care patient. Standard short-term hospital bed-rail protective coverings are not well suited to long-term care patients. Long-term health care beds often times include a bed-rail which includes an elongated outer rail, or top rail, substantially parallel to a bed mattress and a lower rail substantially parallel to, and a spaced distance below, the outer rail. Long-term care patients who have more fragile bones and skin and can be injured easily by coming in contact with hard surfaces, such as the bed-rail, or relatively sharp edges, such as zippers or plastic hook and loop fasteners.

The invention is a bed-rail protective cover for protecting a long-term care patient in a bed which has a bed-rail from contusions, fractures, abrasions and other injuries which result from contact with the bed-rail, or from catching an appendage between the bed and the bed-rail. The protective cover includes: an outer surface composed of a material which is flexible, non-abrasive, and substantially resistant to penetration by an appendage of a person. Ultra soft vinyl is one such material.

The cover is sized to extend an edge of the cover sufficiently over a bed-rail to prevent a patient from inadvertently poking an appendage between the bed and the bed-rail or through a gap between two bed-rail covers. A securing flap extending from one edge of the cover overlaps the other edge when the cover enfolds the bed-rail. The securing flap may include a fastener for securing the cover. If included, the securing fasteners would be located such that risk of inadvertent contact with them is reduced. Lateral tabs may be included to inhibit lateral motion of the cover along the bed-rail. If included, the lateral tabs would also be located such that risk of inadvertent contact is reduced. Preferably, the tabs, or left and right securing flaps, would be located on portions of the inner surface and extend from the left and right edges of the cover, respectively.

One family of embodiments of the cover includes one or more cut-outs to allow access to bed-rail adjustment mechanisms. This allows for rapid lowering of an adjustable or movable bed-rail, should the need arise.

A fill is disposed within the cover which is sufficiently firm and resilient to absorb impacts to the cover and reduce risk of injury to a patient resulting from impacting the bed-rail. Some appropriate fills include foam rubber, foam polystyrene, foam polyurethane, and gels. It will be apparent to those skilled in the art of padding that other fills and combinations, such a gel layer over a foam rubber layer, would be work.

One family of embodiments includes a recessed bed control opening in the cover. The bed control should be sufficiently recessed in the bed control opening to reduce risk of inadvertent contact by a patient with the bed control. This will allow a bed ridden patient convenient access to bed control units, nurse call boxes, and similar devices without increasing the risk of injury.

An objective of this invention is to provide a bed-rail protective cover to provide a safe environment for the recipient of long-term care. The objective includes providing a device to protect the patient from 'hard spots,' or spots where the hardness of the rail would injure the patient. A concurrent object is to reduce the likelihood of 'edge' injury, that is injuries due to the skin being abraded, bruised or lacerated on an edge of the cover or a fastener. A further objective is to maintain protection to a long-term care recipient from 'hard spots' and 'edges' during egress and ingress to the bed, as well as when the patient is in the bed. Another objective of this invention is to reduce risk of 'poke-through,' that is, a limb or digit poking between the bed-rail and the cover, or poking through a gap between two covers, and potentially getting caught. Yet another objective is to provide a covering which is soft, well padded, nonabrasive, cleanable, and moisture resistant. A further objective of this invention is to avoid impediment to rapid lowering of a bed-rail on which the cover is used. Another objective is to make the protective cover quickly and easily attachable and detachable.

DESCRIPTION OF THE PREFERRED EMBODIMENTS

The invention relates generally to bed-rail protective coverings. Specifically the invention relates to bed-rail protective covers for long-term care patients. Long-term care patients often have fragile bones which are more easily injured or skin which is more easily abraded than a short term patient. Bed-rail protective coverings typically used in hospitals for use with long-term care patients. Generally hospital stays are short-term, are for treating illnesses or injuries different from those of long-term care. The necessary equipment and accessories for short- and long-term care facilities are similar, but generally the designs are not optimized for both.

Long-term health care beds often times include a bed-rail which includes an elongated upper rail substantially parallel to a bed mattress and a lower rail substantially parallel to a space distance below the upper rail. Long-term care patients who have more fragile bones and skin and can be injured easily by coming in contact with hard surfaces, such as the bed-rail, or relatively sharp edges, such as zippers or plastic hook and loop fasteners.

Applicants invention will be best understood when considered in light of the following descriptions of the preferred embodiments of the invention as illustrated in the attached drawings wherein like referenced numerals and characters referred to like parts.

Figure 1:
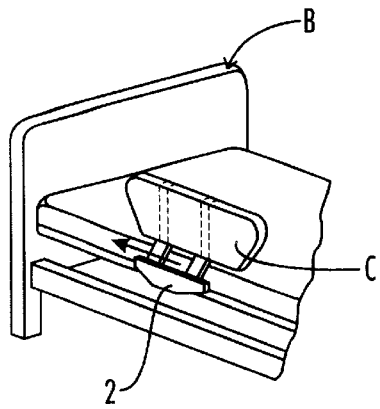
FIG. 1 shows prior art covering a half bed-rail.

FIG. 1 shows a prior art cover C for a bed-rail R on a bed B. As evidenced from FIG. 1 it is possible that a limb or digit might protrude between the bed-rail R and the cover C. Thus risking injury to a patient.

Figure 2:
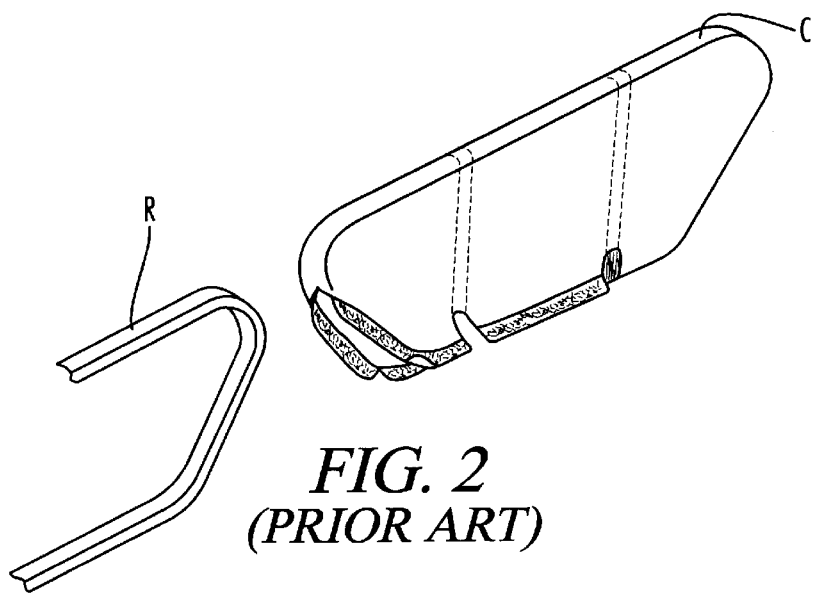
FIG. 2 shows the prior art shown FIG. 1 being slid onto a half bed-rail.

FIG. 2 shows a cover similar the one shown in FIG. 1 being slid laterally onto a bed-rail R. This may be adequate for short bed-rails but is ineffective for long full-length side rails as is typically used in long-term health care.

Figure 3:
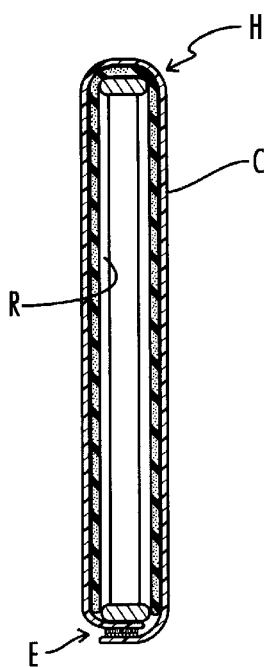
FIG. 3 shows a cross-sectional view of the prior art bed-rail cover shown in FIG. 1.

FIG. 3 shows a cross-sectional view of the cover C shown in FIG. 1. Hard points H at the top and bottom of the bed-rail R can be seen. These are locations where a patient may injure himself. A possible sharp edge E is also shown in FIG. 3.

Figure 4:
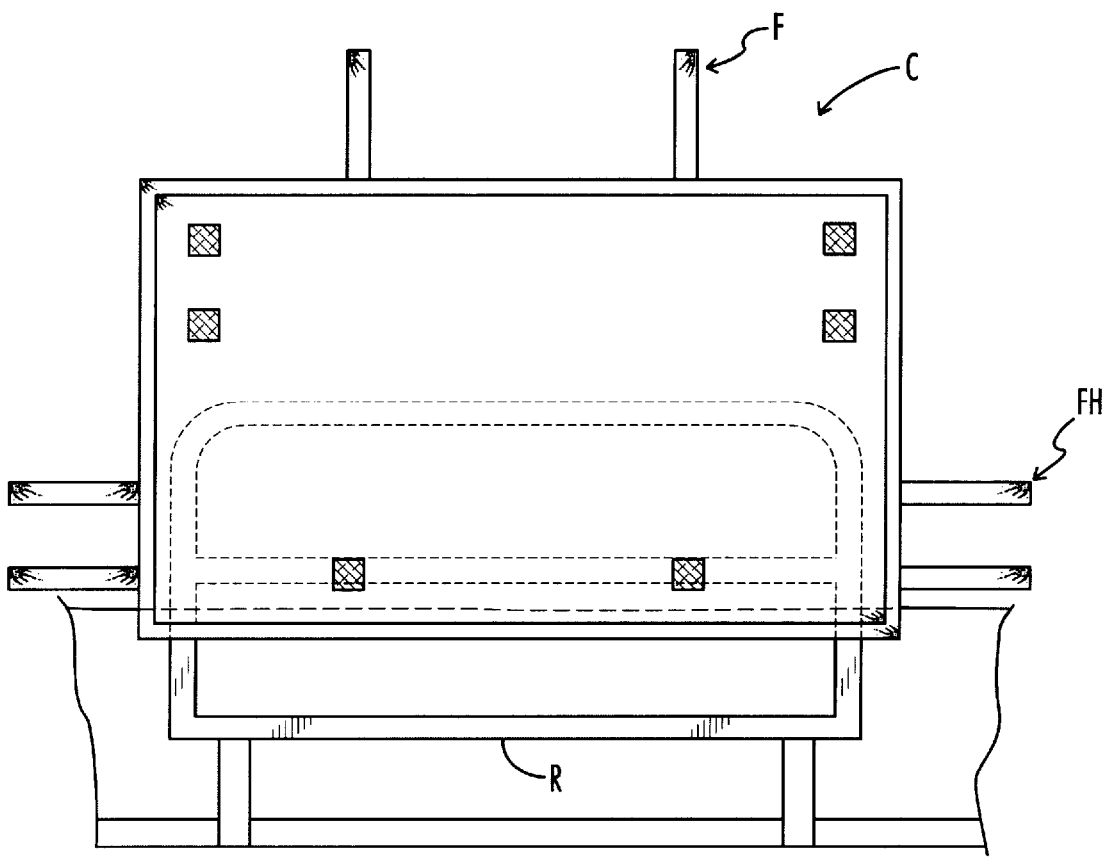
FIG. 4 shows a prior art design for a half bed-rail with fasteners facing a patient.

FIG. 4 shows a prior art protective pad C for a half bed-rail R. This embodiment has fasteners F and horizontal fasteners FH facing the patient. The pad C does not extend sufficiently below the mattress to prevent a digit or limb from getting caught between the mattress and the bed-rail R, or the cover C and the bed-rail R.

Figure 5:
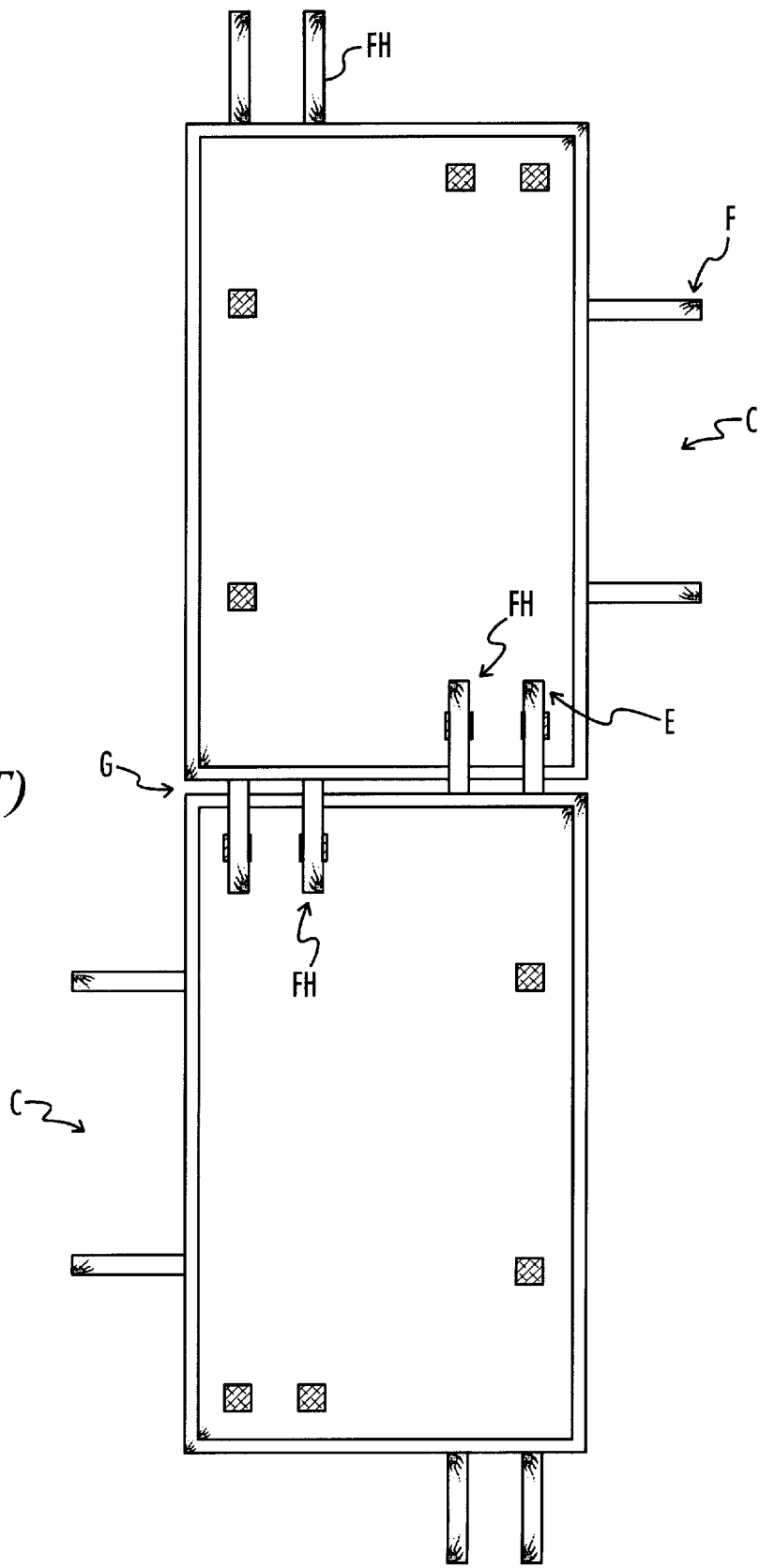
FIG. 5 shows the prior art bed-rail cover of FIG. 4 axially aligned for use with a full-length bed-rail and fastener tabs facing toward a patient.

FIG. 5 shows two pads C, similar to the one depicted in FIG. 4, axially aligned to accommodate full-length bed-rails. A gap g between two covers C, or an overlap of the covers, presents an opportunity for a limb or a digit to poke between the covers C and be caught. This could lead to injuring to a patient. From FIG. 5 it can be seen that the horizontal fasteners FH, used to fasten one cover C to the other cover C, fasten facing towards a patient on a bed B. This should be avoided because the fasteners present the possibility of cuts, scrapes and abrasions from sharp edges E.

Figure 6:
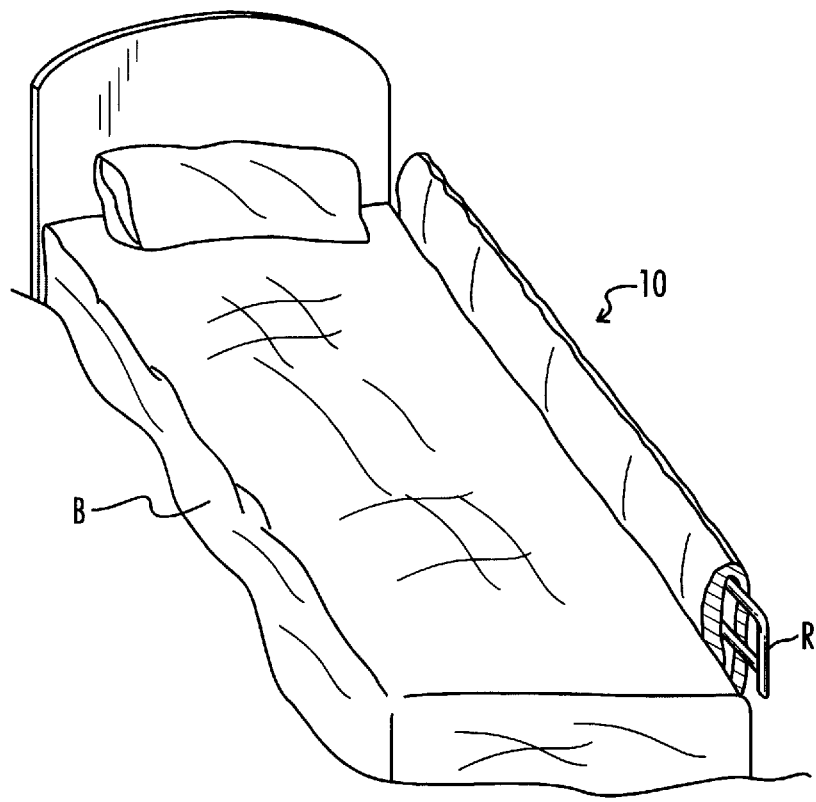
FIG. 6 shows a perspective view of the bed-rail protective cover of this invention for use in long-term care.
Figure 8:
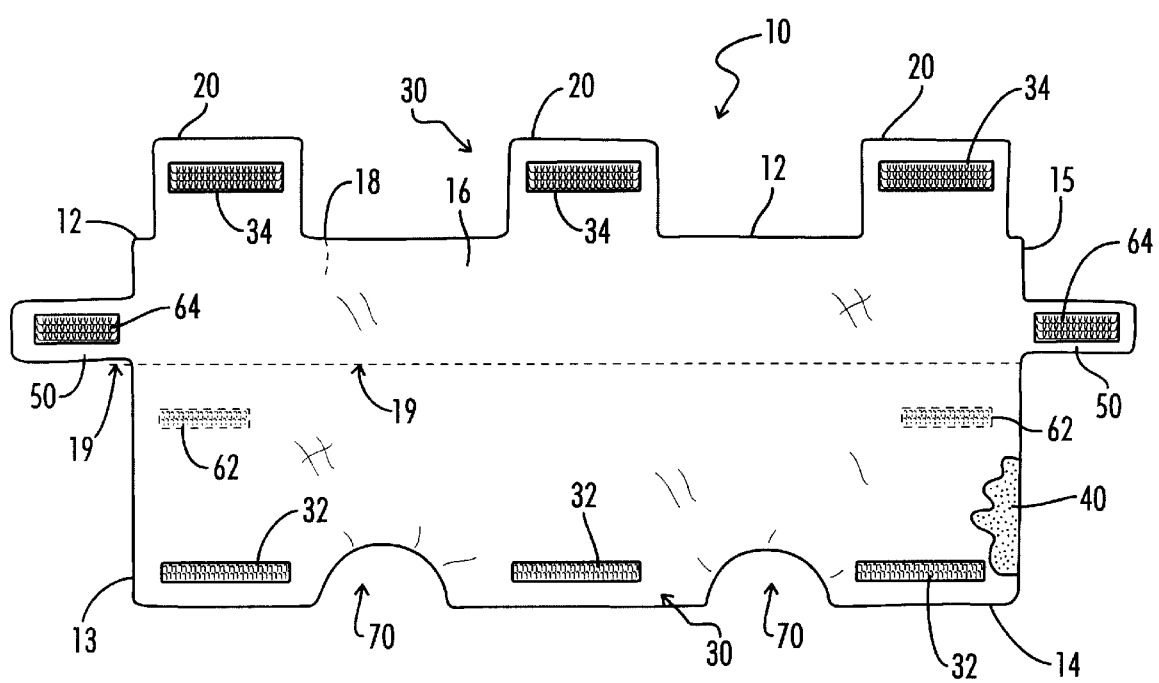
FIG. 8 shows a plan view of a the bed-rail protective cover of FIG. 6, but modified to include bed-rail adjustment mechanism cut-outs.

The invention is shown in FIG. 6. FIG. 6 shows a bed and mattress B with a bed-rail R; wrapped around the bed-rail R is the protective cover 10 of the present invention to prevent a patient from being injured as a result of impacting the bed-rail R. The protective cover 10 extends sufficiently below the bed mattress B so that a patient cannot inadvertently catch his limbs or digits between the mattress B and the bed-rail R. The protective cover 10 has an inner surface 16 and an outer surface 18. The outer surface 18 is exposed. Refer to FIG. 8 for a plan view of the invention more clearly showing the inner surface 16 and other features of the invention.

The protective cover 10 includes a top edge 12, a bottom edge 14, a left edge 13, and a right edge 15. A cover length is defined between the left edge 13 and the right edge 15; a cover width is defined between the top edge 12 and the bottom edge 14. A center fold line 19 runs the cover length and is substantially parallel to the top edge 12. In one embodiment, the cover length is substantially equal to the bed rail length, and the cover width is substantially equal to twice the bed rail width such that when the center fold line 19 sets on the top horizontal rail of a bed rail R, the cover extends over substantially all of the bed rail R.

The outer surface 18 of the cover 10 is sufficiently flexible, resilient and nonabrasive so the patient is not injured by the cover itself. Further, the outer surface 18 of the protective cover 10 should be substantially resistant to penetration by a patient's limb or digit so that a patient cannot inadvertently poke through the cover. Preferably, the outer surface 18 of the cover 10 is cleanable and moisture resistant. A padding, or fill, material 40 is disposed between the inner surface 16 and the outer surface 18.

Figure 7:
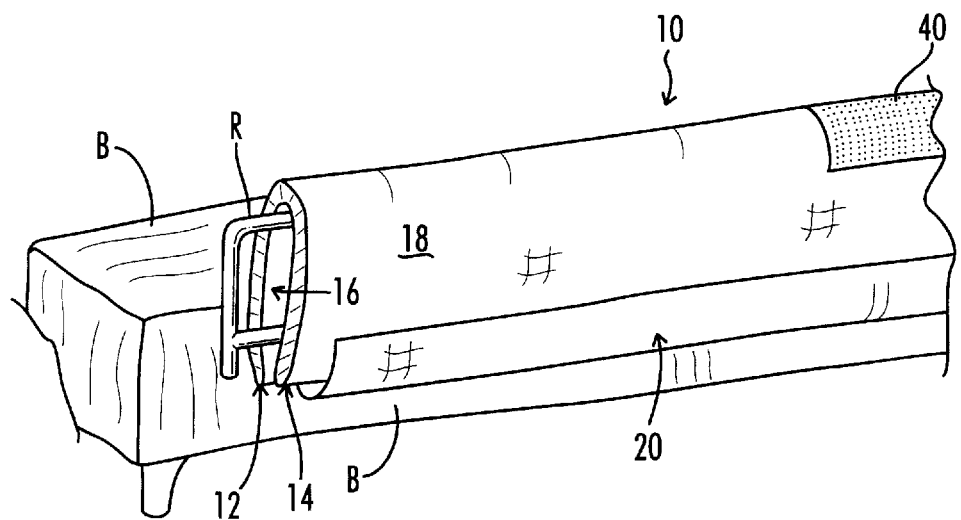
FIG. 7 shows a perspective view of the bed-rail protective cover of FIG. 6, looking from outside the bed.

FIG. 7 shows a perspective view of a cover 10, similar to the one shown in FIG. 6, but from a different orientation than the one shown in FIG. 6. FIG. 7 also shows the top edge 12 protruding sufficiently beyond the edge of the mattress B such that limbs or digits would not protrude between the bed-rail R and the cover 10. A bottom securing flap 20 is also shown. The bottom securing flap 20 secures the protective cover 10 on the side away from a patient so that a patient is not injured by the securing flap 20. Also depicted is a cut-away view showing a filling 40 disposed within the cover 10.

FIG. 8 shows a plan view of an embodiment of the protective cover 10. The inner surface 16 is facing up, and visible; the outer surface 18 is facing down, not visible. A top, or first, edge 12 extends sufficiently beyond the mattress to prevent inadvertent protrusion or catching of a limb or a digit between the bed mattress and the bed rail or the mattress and the cover. Extending from the top edge 12 are bottom securing flaps 20. The bottom securing flaps 20 are secured to a bottom, or second, edge 14 with hook and loop fasteners 32 and 34, respectively. A center fold line 19 runs parallel to the top edge 12 between a left edge 13 and a right edge 15. The cover 10 is sized such that when the center fold line lays upon the top rail of a bed rail R, the cover 10 substantially covers the bed rail R. A cut-away shows a fill 40 disposed within the cover 10.

Tabs, or left and right securing flaps, 50 extend from the left 13 and right 15 edges, respectively, of the cover 10 in an orientation substantially parallel to the bed-rail R. The tabs 50 secure the cover 10 to prevent lateral movement of the cover 10 along the bed-rail R. In some bed-rail configurations, the tabs 50 may be tied to the bed frame or the bed-rail. Preferably, the tabs 50 are secured in place with hook 62 and loop 64 fasteners. The fastener should be located on the inner surface 16 of the cover 10 to reduce risk of contact with, and injury to, a patient. Cut-outs 70 give convenient access to bed-rail R adjustment mechanisms AM (See FIG. 9).

Figure 9:
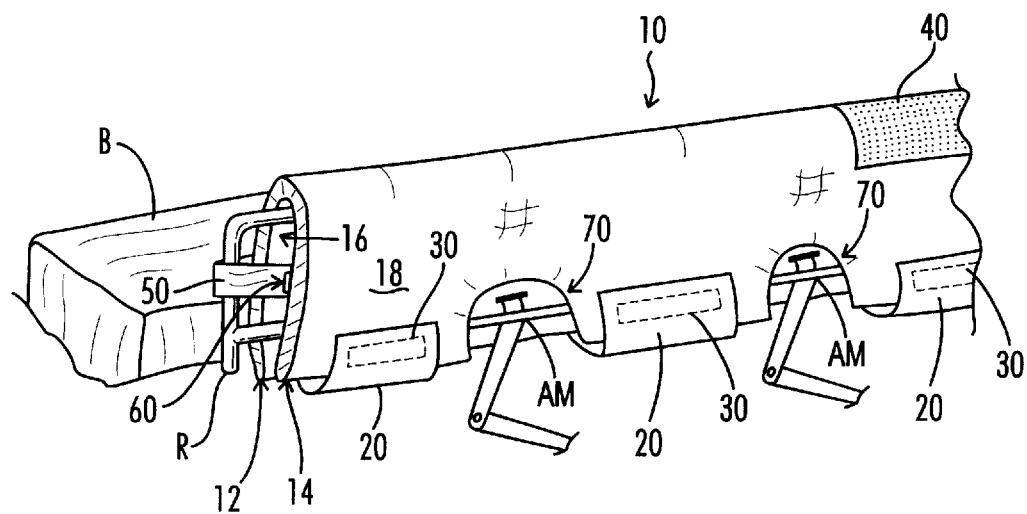
FIG. 9 shows a partial perspective view of the bed-rail protective cover FIG. 8.

FIG. 9 shows a perspective view of the protective cover 10 of FIG. 8 on a bed-rail R mounted on a bed and mattress B. The top edge 12 extends sufficiently below the mattress B to prevent protrusion of the limb or digit by a patient. FIG. 9 shows adjusting mechanisms AM and adjustment mechanism cut-outs 70. Lateral tab fasteners (left and right securing flaps) are generally referenced as 50 and securing bottom flap fasteners are generally referenced as 30.

Figure 10:
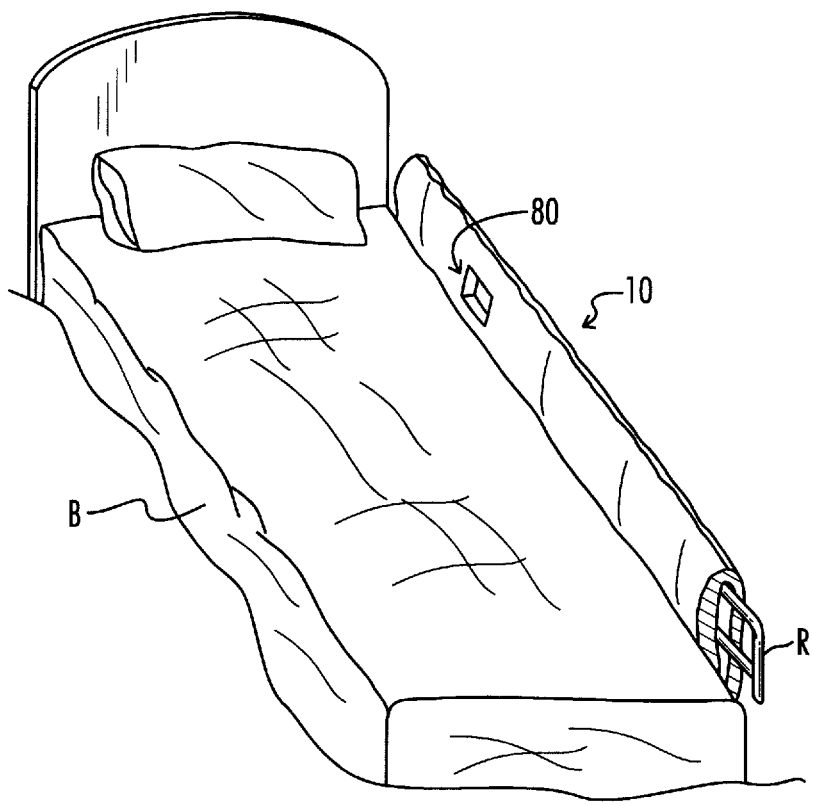
FIG. 10 shows a perspective view of the padded protective cover of FIG. 6, further including a recess for a bed control.

FIG. 10 shows a perspective view of a protective cover 10 similar to the covers shown in FIGS. 6, 7, 8, and 9 further including a bed control opening 80. A bed control (not shown) is sufficiently recessed in the opening such that a patient cannot injure himself by inadvertently impacting with the bed control or another device placed within the bed control opening 80.

In a preferred embodiment, the protective cover includes a cover 10 having an outer surface. The outer surface 18 is flexible, resilient, substantially resistant to penetration by a limb or a digit of a person as well as being nonabrasive, cleanable, and moisture resistant. The cover 10 includes a top edge 12 which extends sufficiently below a height of a mattress on a bed B to prevent an appendage of a person on the bed B from protruding between a mattress and a bed-rail R when the cover wraps around or enfolds the bed-rail R. Two or more bottom securing flaps 20 extend from the top edge 12 to overlap a bottom edge 14. The bottom securing flaps 20 include fasteners 30 for fastening the bottom securing flaps to the bottom edge 14. In the preferred embodiment, the fasteners. 30 include a hook 32 and loop 34 combination. Those skilled in the art of attachments will be aware of other attachment means to secure the cover 10 to the bed rail R, both laterally and vertically.

A padding, or fill, material 40 is disposed within the cover 10 for absorbing impacts to the cover and reducing risk of injury to a patient resulting from impacting a bed-rail R. The fill material 40 is sufficiently firm, flexible and resilient enough to absorb impact to the cover and reduce risk of injury to a patient resulting from impacting a bed-rail R. In a preferred embodiment, the fill material 40 is foam rubber.

To limit lateral movement along the bed-rail R, the preferred embodiment includes tabs left and right securing flaps) extending from the cover, from the respective left 13 and right 15 edges, substantially parallel to the top 12 and bottom 14 edges such that the tabs 50 wrap around the bed-rail R and fasten to the cover 10. The tabs 50 include fasteners 60 comprising a hook 62 and loop 64 combination in the preferred embodiment. The tab fasteners are located so as to reduce risk of inadvertent contact by a patient, thus reducing the possibility that she may be injured by the fasteners.

Also included in a preferred embodiment are bed-rail adjustment mechanism cut-outs 70 along the bottom edge 14 for conveniently accessing a bed-rail R adjustment mechanism AM. This allows for quickly and conveniently raising and lowering the bed-rail R.

A preferred embodiment includes the following, approximate, dimensions. Refer to FIG. 8. The protective cover measures 61 inches by 50 inches. Along one lengthwise edge 14 are two adjustment mechanism cutouts 70 which are mostly semicircular. Each cut out 70 is spaced 16 inches from a widthwise edge 13 and 15. The 'diameter' of the cutouts 70 measure 7.5 inches and the 'radius' of the cutouts 70 measure 4.5 inches. This leaves a separation of 16 inches between the cutouts 70.

Three hook 32 and loop 34 strips (sold under the trade name Velcro) measuring 13 inches by 2 inches are placed along the same edge 14 as the cutouts 70, and spaced about the cutouts 70. Specifically, 1.5 inches from a widthwise edge 13 or 15 or a cutout perimeter.

Three flaps 20 depend from the opposite lengthwise edge 12 in positions corresponding to the three Velcro strips 32 on the lengthwise edge 14 having the adjustment mechanism cutouts 70. The flaps 20 measure 14 inches by 5.5 inches and include the mating Velcro strip 34 on the under side of the flap 20. Thus, when the protective cover 10 folds along the center line on a bed rail R, the flaps 20 can be folded over and up to engage the Velcro strips 32 and secure the protective cover 10 to the bed rail R. One design envisions using foam rubber fill at least 1 inch thick.

Thus, although there have been described particular embodiments of the present invention of a new and useful "Protective Padded Accessory For Use On Long-Term Health Care Bed-Rails," it is not intended that such references be construed as limitations upon the scope of this invention except as set forth in the following claims.

What is claimed is:

1. A bed-rail protective cover for protecting a person in a bed having a bed-rail from contusions, fractures, abrasions and other injuries resulting from contact with a bed-rail or catching an appendage between a bed and a bed-rail, where the bed-rail has a top horizontal rail member having a rail length, and left and right vertical rail members extending downward from the top horizontal rail member to define a rail width, the protective cover comprising:

a. a cover having an inner surface and an exposed outer surface formed of a material the material being flexible, non-abrasive, and substantially resistant to penetration by an appendage of a person;

b. the cover having a center fold line, left and right edges defining a cover width, and top and bottom edges defining a cover length, wherein the cover length is substantially equal to the rail length;

c. the cover width being substantially twice the rail width such that when the cover is installed over the bed rail, the center fold line is proximate the top horizontal rail member and the cover extends over substantially all of the bed rail;

d. the cover further including a first adjustment cut-out extending through the cover and adapted to provide access to a bed-rail adjustment mechanism;

e. the protective cover further comprising a padding fill material between the inner surface and the outer surface; and f. attachment means to attach the cover to the bed rail, the attachment means including at least one bottom securing flap having a first end attached to the top of the cover and a second end removably attachable to the bottom edge of the cover.

2. The bed-rail protective cover of claim 1, wherein the attachment means further comprises a plurality of bottom securing flaps, including the first bottom securing flap, wherein each bottom securing flap has a first end attached to the top edge of the cover and a second end removably attachable to the bottom edge of the cover.

3. The bed-rail protective cover of claim 1, further comprising a plurality of adjustment cut-outs, including the first adjustment cut-out, wherein each adjustment cut-out is adapted to provide access to a bed-rail adjustment mechanism.

4. The bed-rail protective cover of claim 1, wherein the cover includes a control opening facing the bed and located to correspond to a bed control, the control opening adapted to provide a recess for the bed control.

5. The bed-rail protective cover of claim 1, the attachment means further comprising left and right side securing flaps, the left side and right side securing flaps each having a first end attached to first portions of respective left and right edges of the cover and a second end removably attachable to second portions of the respective left and night edges of the of the cover where the left and right side securing flaps extend outside the left and right vertical rail members.

6. The bed-rail protective cover of claim 5, wherein each of the bottom, left, and right securing flaps comprise a hook and loop fastener.

7. The bed-rail protective cover of claim 5, comprising a plurality of adjustment cut-outs, including the first adjustment cut-out.

8. The bed-rail protective cover of claim 5, wherein the cover includes at least one control openings facing the bed and located to correspond to a bed control, the control opening adapted to provide a recess for the bed control.

9. The bed-rail protective cover of claim 8, wherein each of the bottom, left, and right securing flaps comprise a hook and loop fastener.

10. The bed-rail protective cover of claim 1, wherein the inner surface is formed of a slide resistant material.

11. The bed-rail protective cover of claim 1, wherein the fill material comprises a gel.

* * * * *